United States Patent [19]

Cervato

[11] Patent Number: 5,738,124
[45] Date of Patent: Apr. 14, 1998

[54] DENTAL FLOSS HOLDER AND METHOD OF USE THEREOF

[75] Inventor: Aldo Cervato, London, England

[73] Assignee: Harry J. Burns, Kitchener, Canada

[21] Appl. No.: 657,441

[22] Filed: Jun. 3, 1996

[51] Int. Cl.[6] .................................................. A61C 15/00
[52] U.S. Cl. .................... 132/323; 132/329; 206/369; 206/63.5; 206/823
[58] Field of Search ................................. 132/323, 321, 132/329, 324; 206/368, 369, 63.5, 581, 823

[56] References Cited

U.S. PATENT DOCUMENTS

| | | | |
|---|---|---|---|
| 2,187,899 | 1/1940 | Henne | 132/323 |
| 4,253,477 | 3/1981 | Eichman | 132/323 |
| 5,067,503 | 11/1991 | Stile | 132/324 |
| 5,261,430 | 11/1993 | Mochel | 132/323 |
| 5,483,982 | 1/1996 | Bennett et al. | 132/323 |

Primary Examiner—Cary E. O'Connor
Assistant Examiner—Pedro Philogene
Attorney, Agent, or Firm—Daryl W. Schnurr

[57] ABSTRACT

A dental floss holder has a casing containing a cartridge that is slidable within said casing through various sequential positions. The cartridge contains a plurality of U-shaped segments with each segment containing a length of dental floss held across a mouth of the segment in a taut position. As the dental floss is used, the cartridge can be advanced to extend a first segment beyond the cartridge and sever the first segment from the cartridge. The severed first segment is then discarded and the dental floss in the next segment is used. The method is repeated until all of the segments of the cartridge have been used and discarded and a new cartridge is then inserted into the casing.

13 Claims, 6 Drawing Sheets

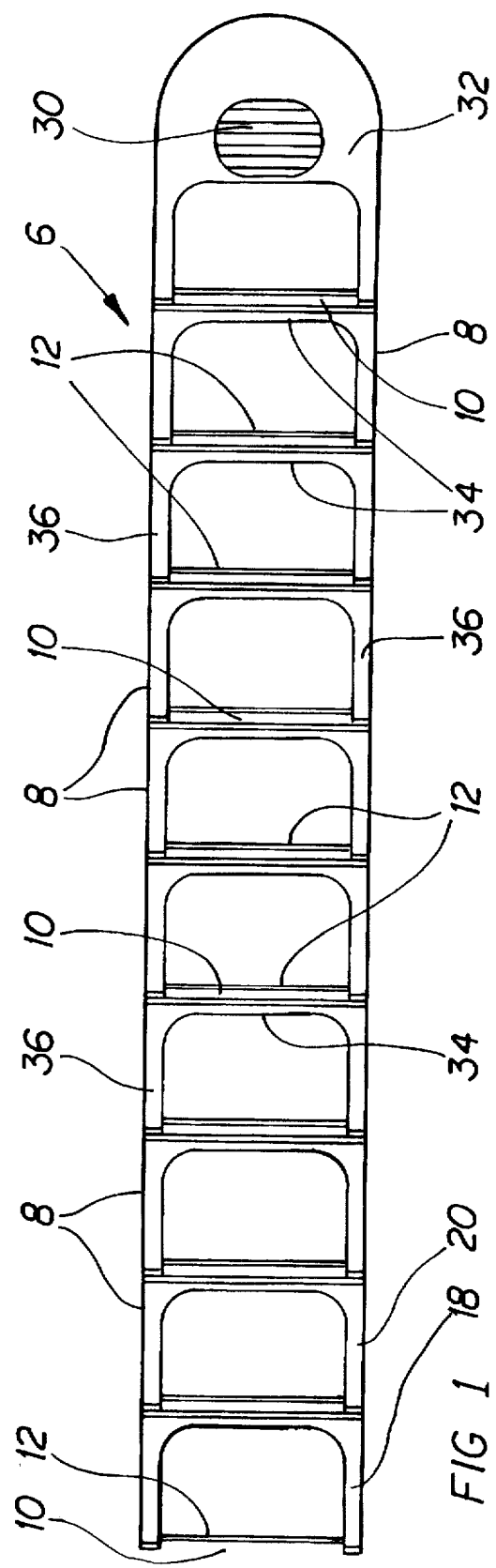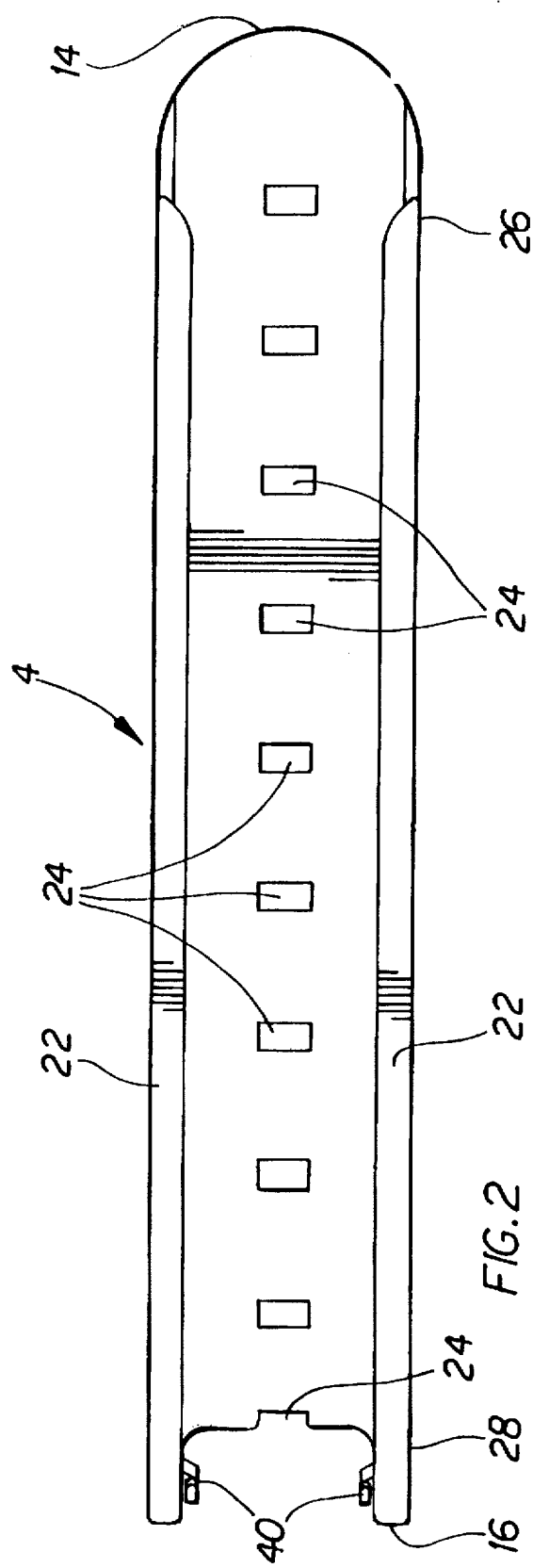

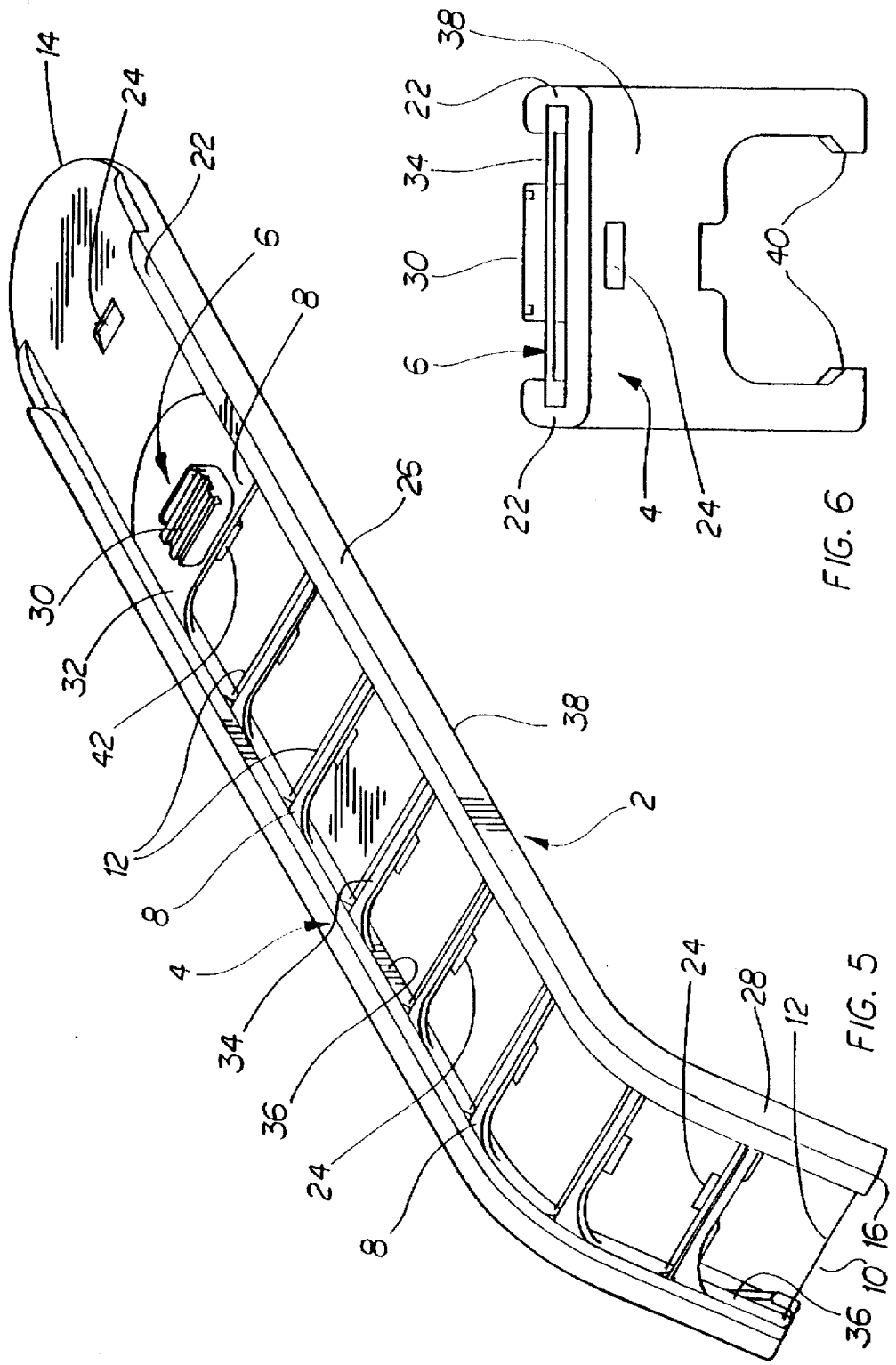

DENTAL FLOSS HOLDER AND METHOD OF USE THEREOF

BACKGROUND OF THE INVENTION

1. Field of the Invention

This invention relates to a dental floss holder and method of use thereof and in particular to a dental floss holder where segments of a cartridge containing dental floss can be broken away for disposal as each segment is successively used.

2. Description of the Prior Art

Numerous dental floss holders are known. Some of the previous holders have a supply of dental floss therein. The floss is threaded into the device for use. After it is used, more floss is threaded into the device from the supply. When the supply is ultimately exhausted, it is replaced with a new supply. Often, to hold the dental floss taut, the floss is wound around an anchor several times to hold the floss in position during use.

In another type of dental floss holder, there are numerous heads containing dental floss. The heads are placed in the holder for use and then discarded after use and replaced with a new head. Dental floss holders are described in U.S. Pat. No. 5,483,982 issued Jan. 16th 1996 to Bennett, et al.; U.S. Pat. No. 5,261,430 issued Nov. 16th, 1993 to Mochel; U.S. Pat. No. 4,941,488 issued Jul. 17th, 1990 to Marxer, et al.; and U.S. Pat. No. 4,253,477 issued. Mar. 3rd, 1981 to Eichman. None of the previous dental floss holders appear to have achieved a significant market share and most dental floss is still used manually by stretching a length of the floss between the fingers of a user.

SUMMARY OF THE INVENTION

It is an object of the present invention to provide a dental floss holder and method of operation thereof whereby the floss is supplied in a cartridge that can be mounted in the holder and subsequently disposed of one segment at a time as the floss in each segment is used.

A dental floss holder has an elongated casing with an input end and an output end. An elongated cartridge has a plurality of interconnected segments, each segment having a mouth with a length of dental floss suspended across said mouth. The casing and cartridge have a corresponding size and shape so that said cartridge is slidable within said casing from said input end to beyond said output end with each of said segments being oriented so that each mouth extends toward said output end. A first segment in said cartridge is a lead segment and each lead segment is severable from said cartridge when it extends beyond said output end.

A method of using dental floss in a holder uses a casing and corresponding cartridge. The holder has an input end and an output end. The cartridge has a plurality of segments attached to one another. Each segment has a mouth with dental floss suspended across said mouth. A lead segment is a first segment in said cartridge. The method comprises the steps of inserting said cartridge into said casing, sliding said cartridge to expose a mouth of said lead segment at said output end, using the dental floss in said lead segment, advancing the cartridge within the casing to extend said lead segment beyond said output end, manually severing said lead segment from said cartridge, thereby exposing a new lead segment which is a second segment of said cartridge, discarding the severed segment and repeating the steps for using the dental floss until all of the segments of said cartridge have been successively used and disposed of, then inserting a new cartridge into said casing and repeating this method.

BRIEF DESCRIPTION OF THE DRAWINGS

In the drawings:

FIG. 1 is a top view of a cartridge;

FIG. 2 is a top view of a casing;

FIG. 5 is a perspective view of a holder with a cartridge advanced to a third position;

FIG. 6 is an end view, from a handle end, of the holder;

DESCRIPTION OF A PREFERRED EMBODIMENT

Figure 3:
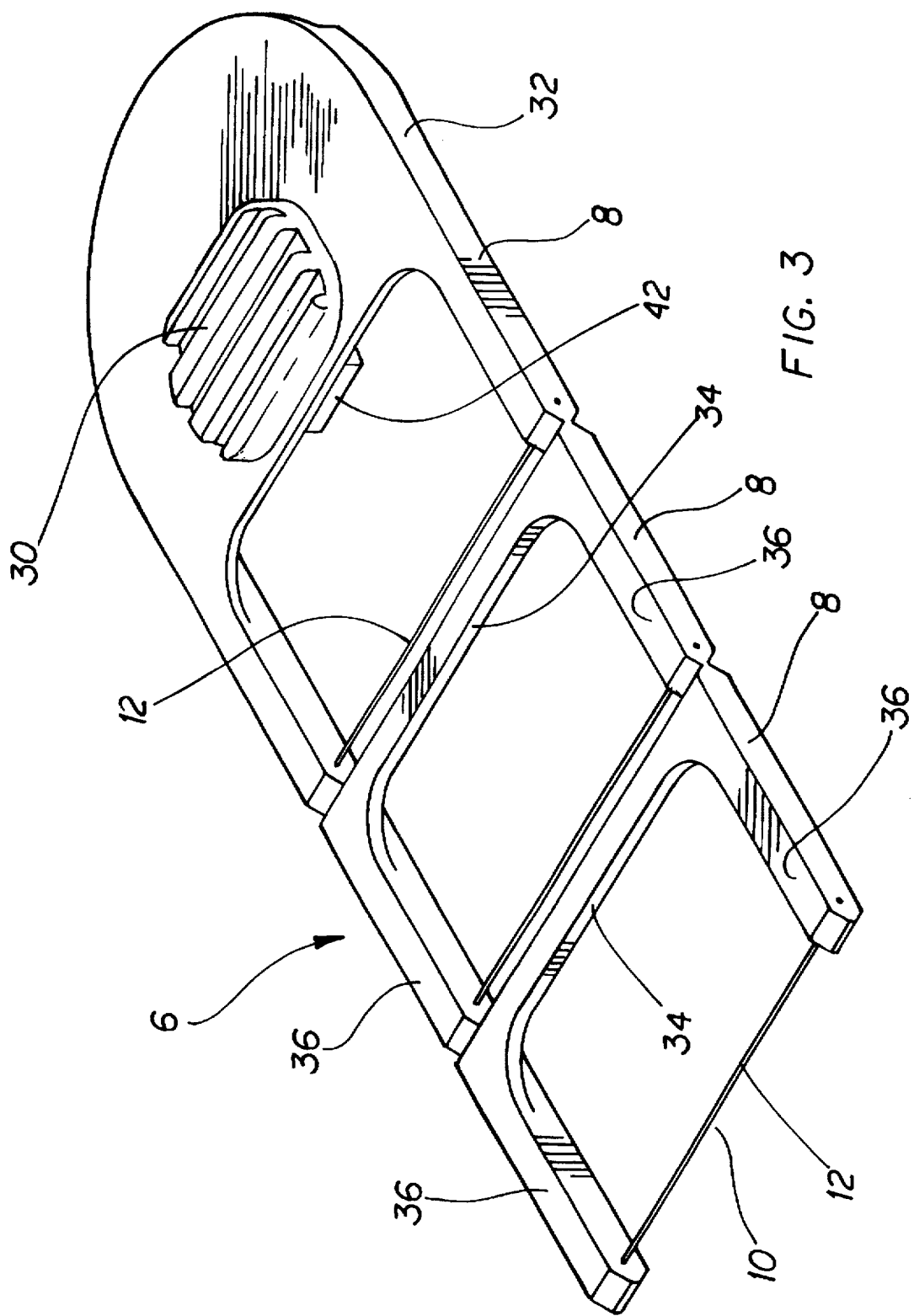
FIG. 3 is a partial perspective view of a cartridge.
Figure 4:
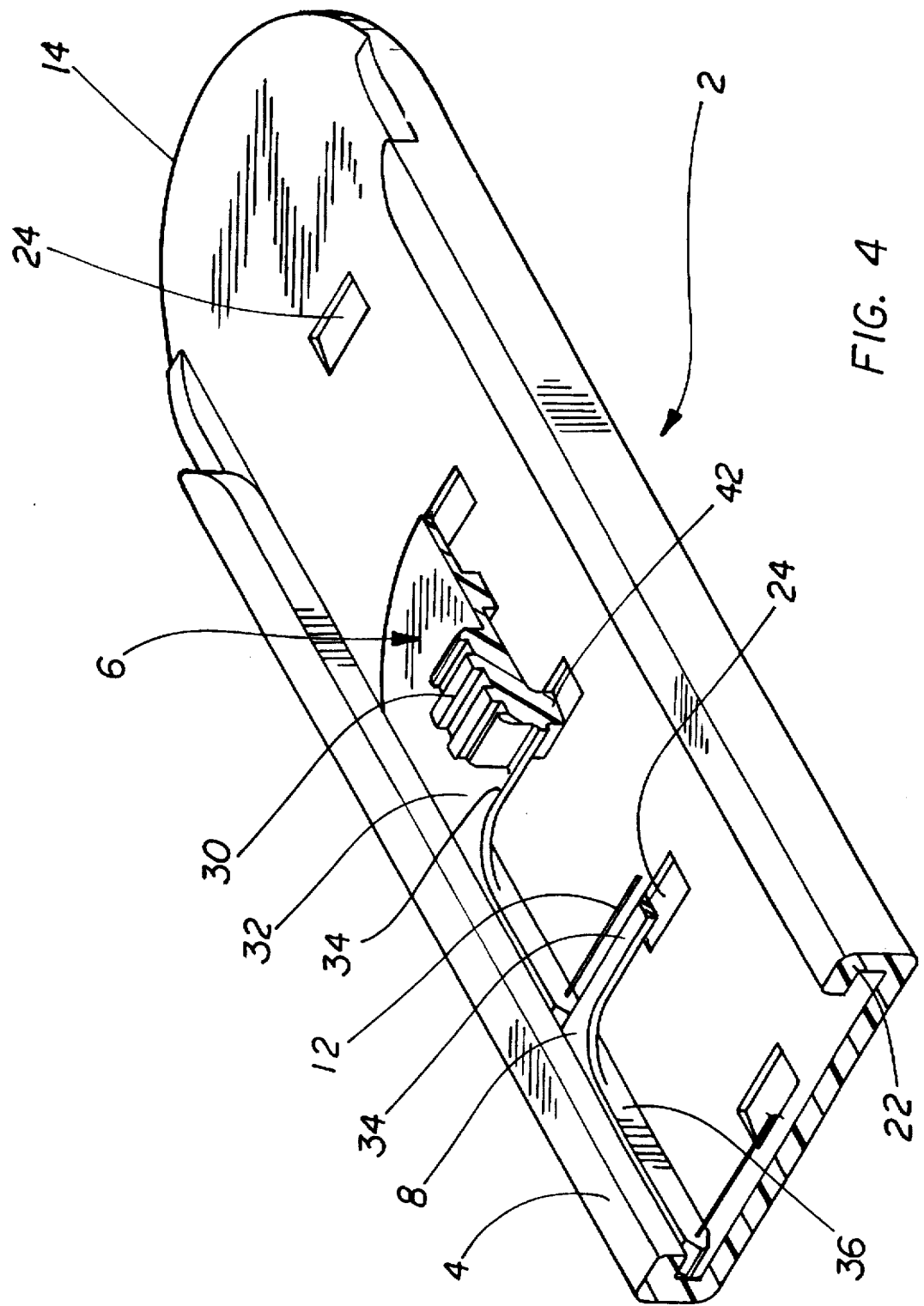
FIG. 4 is a partial perspective view and partial sectional view of a holder.

In FIGS. 1, 2, 3 and 4, a holder 2 has an elongated casing 4 and elongated cartridge 6 slidable therein. The cartridge 6 has a plurality of interconnected segments 8, each segment 8 having a mouth 10 with a length of dental floss 12 suspended across said mouth 10. The casing 4 and cartridge 6 have a corresponding size and shape so that the cartridge 6 is slidable within said casing 4 from an input end 14 to beyond an output end 16 of said casing. Each of said segments 8 are oriented so that each mouth 10 extends towards said output end 16.

A first segment 18 is a lead segment. When a segment extends beyond the output end 16, it can be manually broken away from the remainder of the cartridge, thereby exposing a second segment 20 as the lead segment. This method of severing segments as the cartridge advances through the casing is repeated as the dental floss in each segment is used and each segment is successively discarded. The casing 6 has guide means 22 extending along each side thereof, the casing and cartridge having a corresponding size and shape so that the cartridge is slidable within the casing along said guide means 22 from the input end 14 to beyond the output end 16.

The casing 4 has a series of spaced apart openings 24, the openings being spaced equally from one another by a distance equal to the length of one segment. The casing 4 has a handle 26 at one end and a head 28 at an opposite end. The cartridge 6 has a retention button 30 located therein. Preferably, all of the segments 8 are identical to one another except for a last segment 32, which contains the retention button 30. When the dental floss in the last segment is used, that segment is disposed of along with the retention button 30.

Each segment 8 has a base 34 and two arms 36 extending from said base. The arms 36 form a mouth and the length of dental floss 12 extends across the mouth from one arm to the other. The cartridge 6 shown in FIG. 3 has only three segments 8. The casing 4 shown in FIG. 4 has been cut-off and the cartridge 6 has only two partial segments 8.

In FIG. 5, the cartridge 6 in the holder 2 has been advanced to a third position with the insert 42 of the button located within the third opening 24 from the input end 14. (The second opening 24 is hidden beneath the last segment 32.) In this position the cartridge has only eight segments 8 (rather than ten as shown in FIG. 1) as the first and second segments 18, 20 (not shown in FIG. 5) have been severed and discarded.

From FIG. 5, it can be seen that the holder is curved at the head 28. The connection between the segments 8 is flexible enough so that the segments do not become severed from the cartridge as the cartridge proceeds around the curve. The connection between the segments 8 is brittle enough so that each segment can be severed from the remainder of the cartridge in turn by applying a manual force to each segment as it extends beyond the head.

From FIG. 5, it can further be seen that the retention button 30 has an insert 42 that is sloped from a forward edge. When a rear portion of the button 30 is manually depressed, the button flexes downward in the middle and upward at insert 42. Since the insert has a sloped forward edge, the insert backs out of the opening 24 so that the cartridge can be advanced further into the casing to the next successive position. As the dental floss in each segment is used, the cartridge is advanced and the lead segment is severed from the rest of the cartridge and discarded, thereby exposing a new lead segment. When the dental floss is being used by a user, the user will be holding onto the handle 26 of the casing 4, thereby tending to force the cartridge backward within the casing. A rear edge of the insert 42 will prevent any backward movement.

In FIG. 6, there is shown an end view of the cartridge and holder when viewed from the handle end. An underside 38 of the casing 4 is shown. From FIGS. 4 and 6, it can be seen that the casing has a C-shaped cross-section.

Figure 7:
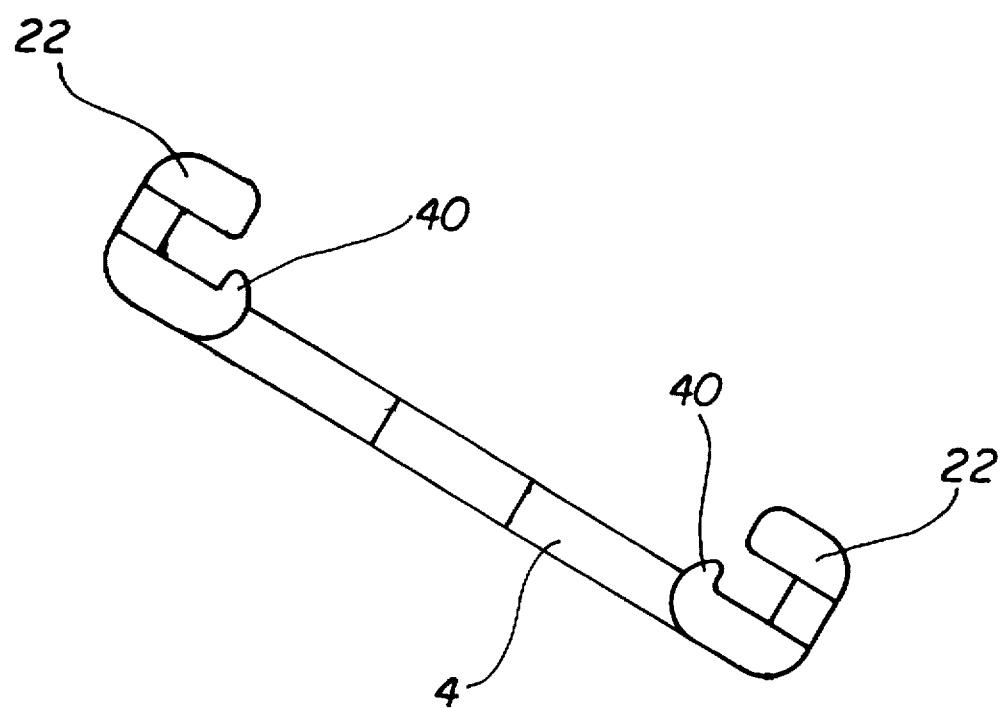
FIG. 7 is an end view of a head of the casing showing projections thereon.

In FIGS. 2 and 7, two projections 40 can be seen at a head 28 of the casing 4. There is one projection 40 on each side of the casing 4. The projections 40 are sized and located to exert outward pressure on the arms 36 of the lead segment. The projections 40 force the arms apart to ensure that the dental floss 12 in that lead segment is taut.

From FIG. 3, it can be seen that the arms 36 of each segment 8 have a greater depth than the base 34. The base 34 is shallower than the arms 36 so that the base 34 will slide over the projections 40. Thus, each segment 8 can easily be extended beyond the output end 16 of the casing.

It can be seen that the last opening 24 (nearest the output end 16) is open on one side. When the insert from the last segment 32 is in this opening, the cartridge will be prevented from moving backward within the casing but will not be prevented from advancing. The casing can be redesigned so that the last opening 24 is closed on all four sides. Then the last segment would be locked in position and prevented from advancing and from moving backward when the insert is located in the last opening.

The retention button 30 and insert 42 could be designed in various different ways. For example, the retention button could contain an elbow therein, the elbow separating a front portion from a rear portion of the button. The insert would be connected to the front portion, which would lie flat and parallel to the casing with the insert inserted into one of the openings 24 when the cartridge is in a locked position within the casing. The button would be spring-mounted to force the button into this locked position. To remove the insert from an opening in the casing, manual force would be applied to the rear portion of the button to force the rear portion into a position where it is essentially parallel with the casing 4. In that position, the insert will be removed from the opening in which it had been located and the cartridge can be manually advanced past that opening. The button can then be released and as the cartridge continues to advance, a spring in the button will cause the insert to snap into the next opening so that the next segment of dental floss can be used. As a further alternative, the button could be designed to be part of the casing so that the button would slide along the casing from position to position and would be connected to the cartridge so that the cartridge would move with the button. If the button were part of the casing, the button would not be discarded as each cartridge is used.

Figure 8:
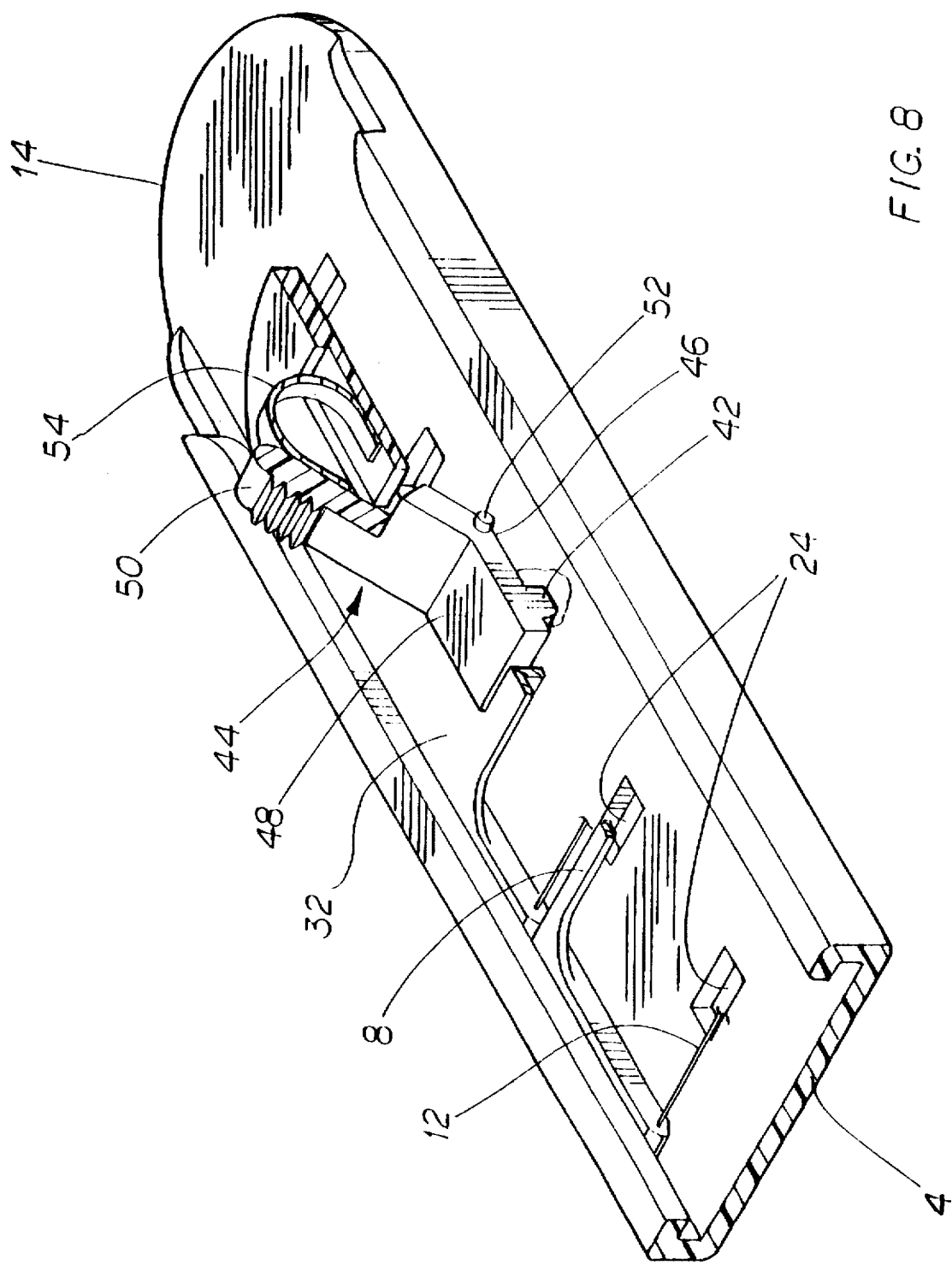
FIG. 8 is a partial perspective view of a holder and cartridge having a spring mounted button.

As shown in FIG. 8, a retention button 44 has an elbow 46 separating a front portion 48 from a rear portion 50. An insert 42 is connected to the front portion 48. In a locked position, the insert 42 is inserted into the opening 24 of the casing 4. The button 44 is mounted in the last segment 32 by protrusions 52 (only one of which is shown), which extend outward from either side of the button 44 at the elbow 46. The protrusions 52 rest in corresponding indentations (not shown) in the segment 32. A spring 54 is located between the rear portion 50 and a surface of the last segment 32. This spring can be virtually of any design. It could be a helical metal spring or it could be a plastic C-shaped spring.

In operation, a cartridge is inserted into the input end of the casing. The cartridge is oriented so that the mouth of each segment extends towards the output end and so that the insert 42 can enter the opening 24 nearest the input end 14. The cartridge is advanced through the casing until the insert on the retention button enters the opening in the casing nearest the input end. In this position, the first segment will be located at the output end of the casing and positioned to enable the dental floss within the holder to be used. The first segment will be the lead segment. After the dental floss in the first segment is used, a downward and forward force is applied to the retention button and the cartridge is advanced (and the button released) so that the insert is located in the second opening from the input end. In this position, the first segment will extend beyond the output end. Manual force is then applied to the first segment to sever it from the rest of the cartridge, thereby exposing the second segment (which will then be the lead segment) at the output end of the casing. This process is repeated until each segment of the cartridge including the last segment 32 has been used. The last segment of the cartridge is then advanced out of the casing and discarded. A replacement cartridge (identical to the cartridge that has just been used) is then inserted and used in the same manner as the previous cartridge. This method can be repeated with the same casing over a long period of time.

The holder of the present invention has several advantages. For example, as each segment is severed and discarded, the next segment is in position for immediate use. Also, it is not necessary to wind, thread or unwind the dental floss as the dental floss is always in place. Further, it is not necessary to change heads each time the dental floss is used as the next available segment moves in the position as part of the process of advancing and discarding the previously used segment. The segments can be stored much more easily as part of the same cartridge than if the segments were separate components.

The width of the holder is somewhat exaggerated in the drawings for ease of illustration. While various different lengths and widths of the holder will be suitable, one size that has been found to be suitable has a width of approximately 5⅞" and a length of approximately 1¹/₃₂". While various materials will be suitable, the cartridge and casing are preferably made from suitable molded plastic materials that are somewhat flexible, yet rigid, and brittle enough that individual segments can easily be severed from the cartridge when desired.

Numerous variations, within the scope of the attached claims, will be readily apparent to those skilled in the art.

What I claim as my invention is:

1. A dental floss holder comprising:
   (a) an elongated casing having an input end and an output end;
   (b) an elongated cartridge having a plurality of interconnected segments, each segment having a mouth with a length of dental floss suspended across said mouth;
   (c) said casing and cartridge having a corresponding size and shape, said cartridge being in position in said casing so that said cartridge is slidable within said casing from said input end to beyond said output end with each of said segments being oriented so that each mouth extends toward said output end; and
   (d) a first segment in said cartridge being a lead segment, each lead segment being severable from said cartridge when each lead segment extends beyond said output end.

2. A dental floss holder as claimed in claim 1 wherein said cartridge and said casing have interlocking means therein to slide said cartridge through sequential positions in said casing.

3. A dental floss holder as claimed in claim 2 wherein said interlocking means is a series of spaced-apart openings in said casing and a release button in said cartridge that is released when depressed, said release button having an insert that extends into one of said openings when the interlocking means is in a locked position.

4. A dental floss holder as claimed in any one of claims 1, 2 or 3 wherein said casing has guide means along each side to receive and guide said cartridge.

5. A dental floss holder as claimed in claim 2 wherein each segment has a U-shape with a base and two arms extending from said base to form said mouth, said dental floss extending across said mouth between said arms.

6. A dental floss holder as claimed in claim 5 wherein each cartridge has projections located at said output end to place outward pressure on said arms, thereby making said floss taut.

7. A dental floss holder as claimed in any one of claims 1, 2 or 3 wherein the casing has a handle at said input end and a head at said output end.

8. A dental floss holder as claimed in any one of claims 1, 2 or 3 wherein the casing is a handle at said input end and a head at said output end and there is a smooth curve in said casing located between said handle and said head.

9. A dental floss holder as claimed in any one of claims 1, 2 or 3 wherein said casing has a C-shaped cross-section.

10. A dental floss holder as claimed in any one of claims 1, 2 or 3 wherein said casing has a curve and said cartridge is sufficiently flexible so that said segments remain attached to one another as said cartridge is moved through said curve of said casing, but sufficiently brittle so that a lead segment can easily be severed from said cartridge when said lead segment extends beyond said casing.

11. A dental floss holder as claimed in claim 3 wherein said button has an elbow between a front portion and a rear portion, said rear portion being at an angle relative to said front portion, said front portion having said insert thereon, said button having a spring to raise said rear portion vis-a-vis said front portion, said button being movable to an open position by manually depressing said rear portion to rock said button on said elbow and thereby raise said front portion.

12. A method of using dental floss in a holder, said holder having a casing and corresponding cartridge, said holder having an input end and an output end, said cartridge having a plurality of segments attached to one another, each segment having a mouth with dental floss suspended across said mouth, a lead segment being a first segment in said cartridge, said method comprising the steps of inserting said cartridge into said casing, sliding said cartridge to expose a mouth of said lead segment at said output end, using the dental floss in said lead segment, advancing the cartridge within said casing to extend said lead segment beyond said output end, manually severing said lead segment from said cartridge, thereby exposing a new lead segment which is a second segment of said cartridge, discarding the severed segment and repeating the steps for using the dental floss until all the segments of a cartridge have been successively used and disposed of, then inserting a new cartridge into said casing and repeating this method.

13. A method as claimed in claim 12 wherein said cartridge and said casing have interlocking means to slide said cartridge through sequential positions in said casing, said interlocking means being released by depressing a release button, said method including the steps of advancing the cartridge within the casing until the interlocking means locks the cartridge in a first position, subsequently depressing the release button to release said cartridge from said first position, advancing the cartridge within said casing and releasing said button, advancing the cartridge until said interlocking means is locked in a second position and repeating the method of depressing the release button, advancing the cartridge and releasing the release button as the dental floss in each segment is used and the segment is ultimately discarded until all of the segments of the cartridge have been discarded, subsequently inserting a new cartridge and repeating the method.

* * * * *